(12) United States Patent
Battistel et al.

(10) Patent No.: US 11,041,178 B2
(45) Date of Patent: Jun. 22, 2021

(54) PROCESS FOR THE PRODUCTION OF SUGARS FROM BIOMASS DERIVED FOR GUAYULE PLANTS

(71) Applicant: VERSALIS S.P.A., San Donato Milanese (IT)

(72) Inventors: Ezio Battistel, Casalino (IT); Egidio Viola, Policoro (IT); Ugo De Corato, Policoro (IT); Giacobbe Braccio, Oria (IT); Valerio Vito, Policoro (IT)

(73) Assignee: VERSALIS S.P.A., San Donato Milanese (IT)

( * ) Notice: Subject to any disclaimer, the term of this patent is extended or adjusted under 35 U.S.C. 154(b) by 0 days.

(21) Appl. No.: 16/760,473

(22) PCT Filed: Oct. 29, 2018

(86) PCT No.: PCT/IB2018/058426
§ 371 (c)(1),
(2) Date: Apr. 30, 2020

(87) PCT Pub. No.: WO2019/087031
PCT Pub. Date: May 9, 2019

(65) Prior Publication Data
US 2020/0347421 A1    Nov. 5, 2020

(30) Foreign Application Priority Data
Oct. 30, 2017 (IT) .................. 102017000123012

(51) Int. Cl.
*C12P 19/02* (2006.01)
*C12P 1/02* (2006.01)

(52) U.S. Cl.
CPC .................. *C12P 19/02* (2013.01); *C12P 1/02* (2013.01); *C12P 2201/00* (2013.01)

(58) Field of Classification Search
CPC ................................ C12P 19/02; C12P 19/14
See application file for complete search history.

(56) References Cited

U.S. PATENT DOCUMENTS

| | | |
|---|---|---|
| 5,628,830 A | 5/1997 | Brink |
| 2013/0130331 A1 | 5/2013 | Binder |
| 2013/0289289 A1 | 10/2013 | Franzosi |
| 2016/0304830 A1* | 10/2016 | Cornish .................. C12P 19/02 |
| 2017/0218094 A1 | 8/2017 | Battistel |

OTHER PUBLICATIONS

International Search Report dated Oct. 2, 2018 for PCT application No. PCT/IB2018/058426.
Written Opinion dated Oct. 2, 2018 for PCT application No. PCT/IB2018/058426.

* cited by examiner

*Primary Examiner* — Tekchand Saidha
(74) *Attorney, Agent, or Firm* — Ohlandt, Greeley, Ruggiero and Perle, LLP

(57) ABSTRACT

Process for the production of sugars from biomass derived from guayule plants comprising: subjecting said biomass to a biological pretreatment in the presence of at least one ligninolytic fungus obtaining a liquid phase comprising sugars and a first solid residue: subjecting said first solid residue to hydrolysis in the presence of at least one diluted inorganic acid obtaining a first hydrolysate comprising sugars and a second solid residue; subjecting said second solid residue to enzymatic hydrolysis obtaining a second hydrolysate comprising sugars and a third solid residue. The sugars thus obtained can be advantageously used as sources of carbon in fermentation processes for producing alcohols (e.g., ethanol, butanol), lipids, diols (e.g., 1,3-propanediol, 1,3-butanediol, 1,4-butanediol, 2,3-butanediol), or in chemical synthesis processes for producing other intermediates or chemical products (e.g., furfural). Said alcohols and lipids can be advantageously used in turn in the production of biofuels (e.g., biodiesel or "green diesel"), which can be used as such, or mixed with other fuels for transportation, while said diols can be used in the production of products such as bio-butadiene which can in turn be used for manufacturing rubbers (e.g., polybutadiene or copolymers thereof). Said uses are particularly important in the case of a biorefinery.

16 Claims, 1 Drawing Sheet

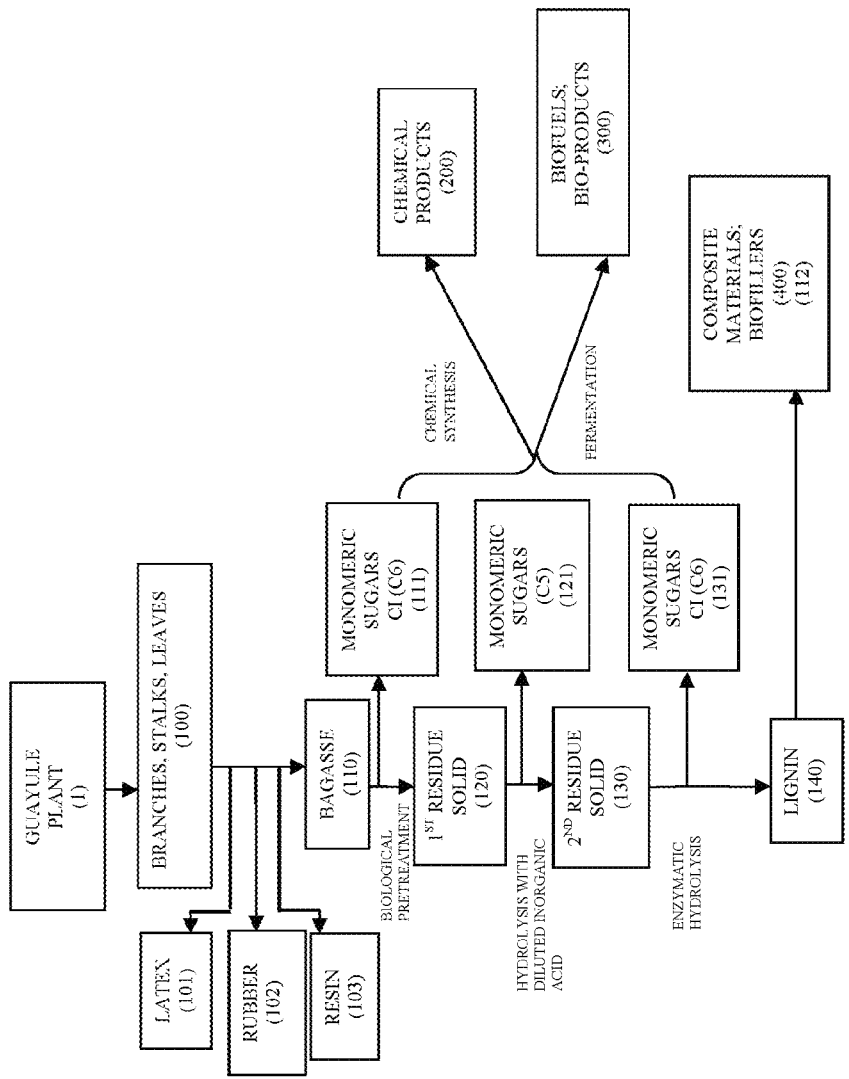

PROCESS FOR THE PRODUCTION OF SUGARS FROM BIOMASS DERIVED FOR GUAYULE PLANTS

CROSS-REFERENCE TO RELATED APPLICATIONS

The present application claims priority on PCT Application No. PCT/IB2018/058426, filed Oct. 29, 2018, which claims priority on Italy Application No. 102017000123012, filed Oct. 30, 2017.

The present invention relates to a process for the production of sugars from biomass derived from guayule plants.

More in particular, the present invention relates to a process for the production of sugars from biomass derived from guayule plants comprising: subjecting said biomass to a biological pretreatment in the presence of at least one ligninolytic fungus obtaining a liquid phase comprising sugars and a first solid residue; subjecting said first solid residue to hydrolysis in the presence of at least one diluted inorganic acid obtaining a first hydrolysate comprising sugars and a second solid residue; subjecting said second solid residue to enzymatic hydrolysis obtaining a second hydrolysate comprising sugars and a third solid residue.

The sugars thus obtained can be advantageously used as sources of carbon in fermentation processes for producing alcohols (e.g., ethanol, butanol), lipids, diols (e.g., 1,3-propanediol, 1,3-butanediol, 1,4-butanediol, 2,3-butanediol), or in chemical synthesis processes for producing other intermediates or chemical products (e.g., furfural). Said alcohols and lipids can be advantageously used in turn in the production of biofuels (e.g., biodiesel or "green diesel"), which can be used as such, or mixed with other fuels for transportation, while said diols can be used in the production of products such as bio-butadiene which can in turn be used for manufacturing rubbers (e.g., polybutadiene or copolymers thereof). Said uses are particularly important in the case of a biorefinery. Natural rubber is a hydrocarbon polymer (cis-1,4-polyisoprene) contained in hundreds of plant species in the form of an aqueous emulsion normally indicated by the term latex. The main source of natural rubber is *Hevea brasiliensis*, a tree native to the Amazon, and South America remained the main source of the limited quantities of latex required throughout the whole of the nineteenth century. Currently, because of parasites and diseases, the American plantations have been almost completely abandoned and the production of natural rubber is almost entirely concentrated in South-East Asia.

To overcome the drawbacks of production that is increasingly exposed to diseases and attack by parasites, over the twentieth century various methods were developed for the production of synthetic rubbers, culminating in the discovery of Ziegler-Natta catalysts that allow isopropene to be polymerized with very high regio- and stereo-selectivity, obtaining a synthetic cis-1,4-polyisoprene that is almost undistinguishable from the one of plant origin. However, natural rubber has never been completely replaced because some of its properties, mainly mechanical, are actually a result of its content of small quantities of lipids and proteins associated with it. Hence, in the total rubber production of 2013 (27.5 Mt), 12 Mt (43%) of natural rubber are still included.

But, the production of rubber from *Hevea brasiliensis* implies some problems of technical and ethical nature. In fact, it is still possible that the same diseases and parasites that destroyed the American plantations also affect the South East Asia ones. Furthermore, the harvesting of the latex requires extensive labor and is only profitable because this labor is paid with extremely low salaries. For these reasons, alternative sources of natural rubber are being investigated. Among these, guayule (*Parthenium argentatum*) is certainly one of the most promising.

Guayule (*Parthenium argentatum*) is a perennial shrub originating in the semidesert regions of the South Western USA (particularly Texas) and Northern Mexico. This plant accumulates natural rubber, mainly comprising the elastomer cis-1,4-polyisoprene, in the form of latex (a milky dispersion or suspension in water) especially in the bark of the branches and of the stem. The natural rubber content can depend on various environmental, farming and preservation factors and is therefore ranging from 5% to 20% of the total weight of the dry plant.

The extraction of natural rubber from guayule plants, as from other plants belonging to the genera of Asteraceae, Euphorbiaceae, Campanulaceae, Labiatae and Moraceae, such as, for example, *Euphorbia lathyris, Parthenium incanum, Chrysothamnus nauseosus, Pedilanthus macrocarpus, Cryptostegia grandiflora, Asclepias syriaca, Asclepias speciosa, Asclepias subulata, Solidago altissima, Solidago gramnifolia, Solidago rigida, Sonchus arvensis, Silphium spp., Cacalia atriplicifolia, Taraxacum koksaghyz, Pycnanthemum incanum, Teucreum canadense, Campanula americana* (indicated in short by the term "guayule type"), represents an important alternative to the extraction of natural rubber from *Hevea brasiliensis*, especially considering the greater resistance of these species to pathogenic agents that attack *Hevea*, the lower import costs of the plant raw material and in virtue of the lower content, in rubbers extracted from these plants compared to that derived from *Hevea*, of numerous proteic contaminants responsible for type I latex allergies (or IgE-mediated).

However, the production of natural rubber from guayule is only profitable if all the other fractions that constitute the plant are also exploited: mainly resin (present in comparable quantities to that of rubber) and the lignocellulosic fraction, as well as small amounts of essential oils and waxes. In particular, after the extraction of the rubber and the resin, widely described in scientific and patent literature, the lignocellulosic residue (bagasse), comprising lignin and polysaccharides, must be subjected to the saccharification process which consists of a hydrolysis of polysaccharides [which are thus transformed into 5-carbon atom (C5) sugars and 6-carbon atom (C6) sugars dissolved in the hydrolysate obtained] that leaves a solid residue containing lignin. The sugars thus obtained can then be used for feeding production processes of organic intermediates by fermentation, while the lignin can be exploited as fuel or in other ways.

Among the saccharification processes described in the prior art the preferable ones are those that allow to obtain the hydrolysis as complete as possible of the hemicellulose and a concentration as high as possible of monomeric sugars with 5 carbon atoms (C5) and monomeric sugars with 6 carbon atoms (C6), at the same time minimizing the formation of oligomers and the formation of reaction subproducts derived from the dehydration of the sugars and from the partial depolymerization of lignin such as, for example, furfural (F), hydroxymethylfurfural (HMF), phenol compounds, which act as growth inhibitors of the microorganisms usually used in the subsequent sugar fermentation processes, determining a substantial reduction in the efficiency and productivity of said processes. Among the processes able to achieve these results, the ones that envisage a pretreatment of the lignocellulosic residue (bagasse) at high temperature or with aggressive chemical substances (for example, with acids or bases), although being effective, can cause problems due to corrosion of the plants, to excessive sugar degradation, to the disposal of toxic or residual substances (for example, salts), etc. As an alternative to said treatments, or for the purpose of reducing the aggressiveness thereof, pretreatment of the lignocellulosic residue (bagasse) through biological methods such as, for example, treatments that envisage the use of fungi able to selectively degrade lignin, may be considered as a valid alternative because of the bland reaction conditions, the simplicity of the technological solutions and the absence of production of toxic substances to be disposed of.

For example, US patent application 2016/0304830 relates to a method for improving the yield of natural rubber from plant material (for example, plant material derived from the guayule plant) through the treatment of an aqueous solution or a suspension (slurry) comprising a plant material, said plant material comprising natural rubber, with a thermophilic fungus, i.e. *Thermomyces lanuginosus*. Said patent application also relates to a method for the saccharification of lignocelluose biomass comprising the following steps: a) providing an aqueous solution or suspension (slurry) comprising lignocellulosic plant material; b) inoculating said aqueous solution or suspension (slurry) with an effective quantity of *Thermomyces lanuginosus* or one or more derivatives thereof; c) incubating said aqueous solution or suspension (slurry) with an effective quantity of *Thermomyces lanuginosus* or one or more derivatives thereof; d) recovering the fermentable sugars obtained from said aqueous solution or suspension (slurry) after the incubation step. The sugars obtained after incubation are mainly monomeric sugars with 5 carbon atoms (C5), such as xylose (42.62%) and arabinose (5%), while the monomeric sugars with 6 atoms (C6) are obtained in small quantities (glucose 5.91%).

Also known are pretreatments of lignocellulosic biomass with ligninolytic fungi which induce the so-called white rot known as "white rot fungi" (WRF). In fact, said fungi, unlike the less selective "brown rot fungi", are able to selectively hydrolyze lignin and therefore to make the polysaccharides contained in the biomass more accessible and more available for subsequent hydrolysis, either of chemical/thermal type, or of enzymatic type, and therefore to improve the final production of monomeric sugars with 5 carbon atoms (C5) and of monomeric sugars with 6 carbon atoms (C6).

For example, Taniguchi M. et al., in the following article: "Evaluation of pretreatment with *Pleurotus ostreatus* for enzymatic hydrolysis of rice straw", published in "Journal of Bioscience and Bioengineering" (2005), Vol. 100, Issue 6, pg. 637-643, describe the pretreatment of rice straw with the white rot fungi (WRF) *Pleurotus ostreatus* before subjecting it to enzymatic hydrolysis. Said pretreatment has led to a degradation of lignin, after 60 days of incubation, equal to 41%. However, at the end of said pretreatment, the production of monomeric sugars with 5 carbon atoms (C5) or of monomeric sugars with 6 carbon atoms (C6) was not highlighted.

Ma F. et al., in the following article: "Combination of biological pretreatment with mild acid pretreatment for enzymatic hydrolysis and ethanol, production from water hyacinth", published in "*Bioresource Technology*" (2010), Vol. 101, pg. 9600-9604, describe a process for improving the enzymatic hydrolysis and the production of ethanol from biomass obtained from water hyacinth (with a particularly low lignin content equal to about 2.8%). For that purpose, said biomass was pretreated with the white rot fungi (WRF) *Echinodontium taxodii* and after 10 days was treated with diluted sulfuric acid (0.25% v/v solution): the residue obtained was subjected to enzymatic hydrolysis obtaining sugars that were subsequently used in the fermentation of the yeast *Saccharomyces cerevisiae* for producing ethanol. The combination of the pretreatment with the white rot fungi (WRF) *Echinodontium taxodii* and diluted sulfuric acid has a synergic effect and allows the yield of sugars to be increased 1.13-2.11 times with respect to the yield of sugars obtained with pretreatment with diluted sulfuric acid alone. The same is valid for the subsequent production of ethanol that shows an increased yield 1.34 times higher than the yield of ethanol obtained with pretreatment with diluted sulfuric acid alone.

Isikhuemhen O. S. et al., in the following article: "Biodegradation and Sugar Release from Canola Plant Biomass by Selected White Rot Fungi", published in "*Advances in Biological Chemistry*" (2014), Vol. 4, pg. 395-406, describe the use of six different white rot fungi (WRF) for pretreating the canals plant. It has been observed that monomeric sugars, including glucose, are released into the culture means, together with exopolysaccharides: the quantity of monomeric sugars obtained was on average 2 g-3 g per 100 g of biomass.

International patent application WO 2016/062753 in the name of the Applicant, relates to an integrated process for the transformation and exploitation of every part of the guayule plant, comprising the following steps in sequence:

separating the stem from the leaves of said plant with a mechanical treatment;

treating the leaves for producing waxes and essential oils, and a fraction comprising cellulose, hemicellulose and to a smaller extent salts, organic compounds and lignin;

extracting from the stem and branches a liquid phase thus forming a first solid woody residue, indicated as bagasse;

treating said first solid woody residue to form sugars, cellulose, hemicellulose and lignin.

The aforementioned integrated process is said to be able to further exploit the guayule plant by adding to the production of latex, rubber, resin and bagasse, also the production of fermentable sugars: said exploitation is particularly important in the case of biorefineries designed to produce organic intermediates other than ethanol, for example, for producing 1,3-butanediol which can be transformed, after its double catalytic dehydration, into bio-butadiene. The production of fermentable sugars is carried out through a saccharification process in two stages: in the first stage, acid hydrolysis is carried out to transform lignin into monomeric sugars with 5 carbon atoms (C5), while in the second stage enzymatic, chemical or thermochemical hydrolysis is carried out, for the purpose of obtaining monomeric sugars with 6 carbon atoms (C6). No reference is made to any biological pretreatments of the biomass derived from guayule plants.

A biorefinery based on the exploitation of all the components obtainable from the guayule plant will be more sustainable the more possible it is to transform the residual lignocellulosic biomass obtained after the extraction of the main components, i.e. latex, resin and rubber (i.e. the bagasse) into monomeric sugars with five carbon atoms (C5) or into monomeric sugars with six carbon atoms (C6) (i.e. second generation sugars). It is known that, while the use of monomeric sugars with 6 carbon atoms (C6) for producing organic compounds (for example, ethanol) does not constitute a problem, the same cannot be said in the case of monomeric sugars with 5 carbon atoms (C5). The reason can be found in the fact that monomeric sugars with 5 carbon atoms (C5) are metabolically less efficient than monomeric sugars with 6 carbon atoms (C6) as they follow catabolic pathways that are partially different. Monomeric sugars with 6 carbon atoms (C6), such as glucose, are catabolized according to the glycolytic pathway, whereas monomeric sugars with 5 carbon atoms (C5), such as xylose, enter into the cell metabolism according to the phosphate pentose pathway and only subsequently join the final part of the glycolytic pathway: said difference in the catabolic pathway leads to the consumption of monomeric sugars with 5 carbon atoms (C5), by many microorganisms, with clearly slower kinetics than those observed in the consumption of monomeric sugars with 6 carbon atoms (C6). Microorganisms even exist, and are used in the microbiological industry, that are not able to use monomeric sugars with 5 carbon atoms (C5).

Therefore, in general, the mixtures of sugars obtained in many hydrolysis processes of biomass comprising both monomeric sugars with 6 carbon atoms (C6), and monomeric sugars with 5 carbon atoms (C5), do not constitute a suitable feeding for many fermentations, except for the traditional alcoholic fermentation carried out in the presence of strains of *Saccharomyces cerevisiae*, appropriately genetically modified, for the purpose of producing ethanol and that are notoriously rather tolerant in relation to the feeding quality.

Therefore, the production of hydrolysates with a prevalent content of monomeric sugars with 5 carbon atoms (C5) constitutes a problem, in particular in the case of biorefineries designed to produce organic intermediates other than ethanol, for example, for producing 1,3-butanediol that can be transformed, after its double catalytic dehydration, into bio-butadiene.

The Applicant therefore set out to solve the problem of increasing the quantity of sugars obtained from the treatment of biomass derived from guayule plants, in particular the quantity of monomeric sugars with 6 carbon atoms (C6), for the purpose of producing organic intermediates other than ethanol.

The Applicant has now found that the quantity of sugars obtained from the treatment of biomass derived from guayule plants, in particular the quantity of monomeric sugars with 6 carbon atoms (C6), can be increased by subjecting the biomass derived from guayule plants to a pretreatment in the presence of at least one ligninolytic fungus obtaining a liquid phase comprising sugars and a first solid residue; subjecting said first solid residue to hydrolysis in the presence of at least one diluted inorganic acid obtaining a first hydrolysate comprising sugars and a second solid residue; subjecting said second solid residue to enzymatic hydrolysis obtaining a second hydrolysate comprising sugars and a third solid residue. The sugars thus obtained can be advantageously used as sources of carbon in fermentation processes for producing alcohols (e.g., ethanol, butanol), lipids, diols (e.g., 1,3-propanediol, 1,3-butanediol, 1,4-butanediol, 2,3-butanediol), or in chemical synthesis processes for producing other intermediates or chemical products (e.g., furfural). Said alcohols and lipids can be advantageously used in turn in the production of biofuels (e.g., biodiesel or "green diesel"), which can be used as such, or mixed with other fuels for transportation, while said diols can be used in the production of products such as bio-butadiene that can in turn be used for manufacturing rubbers (e.g., polybutadiene or copolymers thereof). Said uses are particularly important in the case of a biorefinery.

Numerous advantages are obtained through the process according to the present invention such as, for example:

biological pretreatment with at least one ligninolytic fungus, in particular with a fungus selected from white rot fungi (WRF), allows monomeric sugars with 6 carbon atoms (C6) to be released in the culture medium, mainly glucose, obtained from the metabolic transformation carried out by said ligninolytic fungus of some biomass components directly into soluble monomeric sugars, in particular, glucose can be obtained in quantities equal to 28 g/100 g of bagasse (as stated in the following examples);

the hydrolysis treatment of the first solid residue with at least one diluted inorganic acid, in particular with diluted sulfuric acid, allows almost quantitative hydrolysis of the hemicellulose contained in the biomass to be obtained, mainly producing monomeric sugars with 5 carbon atoms (C5), more in particular, said quantitative yield is obtained using half the amount of diluted inorganic acid, with respect to the case in which the biological pretreatment of the biomass is not carried out;

the enzymatic hydrolysis of the second solid residue allows the cellulose still contained to be hydrolyzed, prevalently obtaining monomeric sugars with 6 carbon atoms (C6), in particular glucose, said yield being higher than the case in which the biological pretreatment of the biomass is not carried out;

said process allows a yield of monomeric sugars with 5 carbon atoms (C5) and monomeric sugars with 6 carbon atoms (C6) to be obtained of about 50 g/100 g of bagasse (dry weight), said yield being clearly higher than that obtained without the biological pretreatment of the bagasse equal to 22 g/100 g of bagasse (dry weight) (as stated in the following examples).

Therefore, the present invention relates to a process for the production of sugars from biomass derived from guayule plants comprising:

subjecting said biomass to a biological pretreatment in the presence of at least one ligninolytic fungus obtaining a liquid phase comprising sugars and a first solid residue;

subjecting said first solid residue to hydrolysis in the presence of at least one diluted inorganic acid obtaining a first hydrolysate comprising sugars and a second solid residue;

subjecting said second solid residue to enzymatic hydrolysis obtaining a second hydrolysate comprising sugars and a third solid residue.

For the purpose of the present description and of the following claims, the definitions of the numeric ranges always include the extremes unless specified otherwise.

For the purpose of the present description and of the following claims, the term "comprising" also includes the terms "which essentially consists of" or "which consists of".

For the purpose of the present description and of the following claims, "guayule plant" generally means both the *Parthenium argentatum* species and guayule type plants of the species listed above.

For the purpose of the present description and of the following claims "monomeric sugars with 5 carbon atoms (C5)" means pentose sugars, or more simply pentoses, which are monosaccharides comprising five carbon atoms having chemical formula $C_5H_{10}O_5$. Likewise, for the purpose of the present description and of the following claims "monomeric sugars with 6 carbon atoms (C6)" means hexose sugars, or more simply hexoses, which are monosaccharides comprising six carbon atoms having chemical formula $C_6H_{12}O_6$.

For the purpose of the present description and of the following claims, the term "biomass derived from guayule plants" means any form (for example, the whole plant, parts of the plant, including roots, branches and/or stems, leaves, any bark, fragments of plant obtained by chopping, grinding, etc., briquettes and pellets obtained by compacting plant fragments) wherein the guayule plant is used for the purpose of obtaining, by means of chemical and/or physical methods, latex, rubber, resin, bagasse, sugars and the other components present in the plant itself.

For the purpose of the present description and of the following claims, the term "bagasse" means the residual portion of plant material derived from the extraction processes to which the guayule can be subjected. The bagasse may also include some quantities of non-plant material for example, soil, sand, etc.) typically associated with the roots of the plants and derived from the cultivation land.

For the purpose of the present description and of the following claims, the term "miscella" means a solution, a suspension or an emulsion consisting of latex, rubber and/or resin, water and/or organic solvents in which the extraction process is carried out, obtained after separation of the bagasse.

According to a preferred embodiment of the present invention, said biomass derived from guayule plants is the bagasse derived from the extraction processes to which said guayule plants are subjected.

Extraction processes to which the guayule plants can be subjected for the purpose of obtaining bagasse are known in the state of the art. For the purpose of the present invention, preferably, said bagasse can be obtained through the process described in international patent application WO 2016/062753 in the name of the Applicant, reported above, incorporated herein for reference purposes.

According to a preferred embodiment of the present invention, said at least one ligninolytic fungus can be selected, for example, from the white rot fungi (WRF) belonging to the strains *Pleurotus ostreatus, Formitiporia mediterranea*.

In accordance with a particularly preferred embodiment of the present invention, said ligninolytic fungus can be selected, for example, from: *Pleurotus ostreatus* MUCL 29420, *Formitiporia mediterranea* MUCL 45670, obtained from BCCM (BE) Belgian Coordinated Collection of Microorganism, Agro-food & Environmental fungal collection MUCL.

For the purpose of the present invention, an inoculum is prepared with said ligninolytic fungus, according to processes known in the state of the art, in the presence of culture media comprising glucose and various nutrients such as, for example, nitrogen, potassium phosphate, magnesium, salts, vitamins, changing gradually to increasingly minimal culture media (i.e. containing an increasingly lower concentration of macronutrients that can be readily assimilated by the ligninolytic fungus such as, for example, carbon, nitrogen, phosphorus), on going from one sub-culture to the next. Subsequently, an aliquot (5 ml) of the culture thus obtained is transferred, operating under sterile conditions, to a 500 ml flask containing 100 g of kernels of soft wheat, which is kept, under stirring, until the fungal mycelium has covered the entire mass of wheat kernels. The flask is then placed under a laminar flow cabinet, for the purpose of drying the mass obtained, which is then finely ground obtaining a wheat flour contaminated with fungi and used for the pretreatment of the biomass (as stated in the following examples). In accordance with a preferred embodiment of the present invention, said biological pretreatment can be carried out at a temperature ranging from 20° C. to 40° C., preferably ranging from 23° C. to 35° C.

In accordance with a preferred embodiment of the present invention, said biological pretreatment can be carried out for a time ranging from 5 days to 25 days, preferably ranging from 10 days to 20 days.

In accordance with a preferred embodiment of the present invention, said biological pretreatment can be carried out at a pH ranging from 4.5 to 7, preferably ranging from 5 to 6.7.

From the biological pretreatment of said biomass, a suspension is obtained comprising a solid phase (i.e. first solid residue) and an aqueous phase (i.e. liquid phase comprising sugars). Said suspension is subjected to filtration or centrifugation for the purpose of obtaining a solid phase, i.e. a first solid residue comprising lignin, cellulose and cells of the ligninolytic fungus (mycelium) and an aqueous phase, i.e. liquid phase comprising sugars.

It is to be noted that the sugars contained in said liquid phases, in particular monomeric sugars with 6 carbon atoms (C6), more particularly glucose, derive from the metabolic activity of the ligninolytic fungus.

In accordance with a preferred embodiment of the present invention, said diluted inorganic acid can be selected, for example, from sulfuric acid, phosphoric acid, or mixtures thereof. Preferably, said diluted inorganic acid is diluted sulfuric acid, even more preferably it is a 2.5% by weight aqueous solution of sulfuric acid.

In accordance with a preferred embodiment of the present invention, said hydrolysis in the presence of at least one diluted inorganic acid can be carried out for a time ranging from 30 minutes to 120 minutes, preferably ranging from 45 minutes to 90 minutes.

In accordance with a preferred embodiment of the present invention, said hydrolysis in the presence of at least one diluted inorganic acid can be carried out at a temperature ranging from 110° C. to 160° C., preferably ranging from 110° C. to 130° C.

In accordance with a preferred embodiment of the present invention, said hydrolysis in the presence of at least one diluted inorganic acid can be carried out at a pH ranging from 0.05 to 2, preferably ranging from 0.08 to 1.0.

From the hydrolysis of said first solid residue, a mixture is obtained comprising a solid phase (i.e. a second solid residue) and an aqueous phase (i.e. a first hydrolysate). Said mixture is subjected to filtration or centrifugation for the purpose of obtaining a solid phase, i.e. a second solid residue comprising lignin and cellulose and an aqueous phase, i.e. a first hydrolysate prevalently comprising monomeric sugars with 5 carbon atoms (C5).

It is to be noted that the sugars contained in said first hydrolysate, in particular monomeric sugars with 5 carbon atoms (C5), more particularly xylose, derive from the hydrolysis of the hemicellulose contained in said first solid residue.

The enzymatic hydrolysis of said second solid residue comprising lignin and cellulose, can be carried out according to techniques known in the state of the art as described, for example, in U.S. Pat. Nos. 5,628,830, 5,916,780 and 6,090,595, using commercial enzymes such as, for example, Cellic® CTec2 by Novozymes Bioenergy, Celluclast 1.5L (Novozymes), Econase CE (Rohm Enzymes), Spezyme (Genecor), Novozym 188 (Novozymes), used individually or mixed together. From the enzymatic hydrolysis of said second solid residue, a mixture is obtained comprising a solid phase (i.e. a third solid residue) and an aqueous phase (i.e. a second hydrolysate). Said mixture is subjected to filtration or centrifugation for the purpose of obtaining a solid phase, i.e. a third solid residue comprising lignin and cellulose and an aqueous phase, i.e. a second hydrolysate prevalently comprising monomeric sugars with 6 carbon atoms (C6), in particular glucose, derived from the hydrolysis of cellulose.

The sugars thus obtained can be advantageously used as sources of carbon in fermentation processes for producing alcohols (e.g., ethanol, butanol), lipids, dials (e.g., 1,3-propanediol, 1,3-butanediol, 1,4-butanediol, 2,3-butanediol), or in chemical synthesis processes for producing other intermediates or chemical products (e.g., furfural). Said alcohols and lipids can be advantageously used in turn in the production of biofuels (e.g., biodiesel or "green diesel"), which can be used as such, or mixed with other fuels for transportation, while said diols can be used in the production of products such as bio-butadiene that can in turn be used for manufacturing rubbers (e.g., polybutadiene or copolymers thereof). Said uses are particularly important in the case of a biorefinery. Lignin can be exploited as a fuel, or for preparing composite materials (for example, after being finely ground, lignin can be dispersed in appropriate synthetic polymers, such as, for example, polyethylene, polystyrene) or as biofillers (for example, after being finely ground, lignin can be dispersed in rubber compounds).

The quantities of sugars obtained after hydrolysis can be determiners through techniques known in the state of the art such as, for example, high performance liquid chromatography (HPLC), or ion exchange chromatography.

The present invention will now be illustrated in more detail through an embodiment with reference to FIG. 1 described below.

FIG. 1 depicts an embodiment of the process according to the present invention. For that purpose, from the guayule plant (1) branches, stems and leaves (100) are separated, for example, through a mechanical treatment. The branches, stems and leaves (100) are subjected to extraction, for example, in the presence of a basic aqueous solution (not shown in FIG. 1) obtaining a first miscella from which latex (101) is extracted and a first bagasse without latex (not shown in FIG. 1). Said first bagasse without latex is subjected to extraction, for example, in the presence of a polar solvent system (not shown in FIG. 1) obtaining a second miscella from which resin (103) is extracted and a second bagasse without latex and without resin (not shown in FIG. 1). Said second bagasse without latex and without resin is subjected to extraction, for example, in the presence of a non-polar solvent system (not shown in FIG. 1) obtaining a third miscella from which rubber (102) is extracted and a third bagasse without latex, without resin and without rubber (110). The bagasse (110) is subjected to a biological pretreatment in the presence of at least one ligninolytic fungus selected from the white rot fungi (WRF) belonging to the strains *Pleurotus ostreatus* or *Formitiporia mediterranea*, obtaining a liquid phase (111) comprising monomeric sugars with 6 carbon atoms (C6), in particular glucose, and a first solid residue (120). Said first solid residue (120) is subjected to hydrolysis in the presence of at least one diluted inorganic acid (for example, in the presence of diluted sulfuric acid) obtaining a first hydrolysate (121) prevalently comprising monomeric sugars with 5 carbon atoms (C5) and a second solid residue (130). Said second solid residue (130) is subjected to enzymatic hydrolysis obtaining a second hydrolysate (131) prevalently comprising monomeric sugars with 6 carbon atoms (C6), in particular glucose, and a third solid residue (140) (indicated as lignin in FIG. 1). Lignin (140) may be conveniently used for preparing composite materials or biofillers (400). Hydrolysates comprising monomeric sugars (111), (121) and (131), can be used in the preparation, via fermentation, of bio-products (300), (such as, for example, bio-butanediols) or biofuels (such as, for example, microbial oils or ethanol) (300), or in the preparation, via chemical synthesis, of chemical products (200) (such as, for example, furfural).

More details on obtaining said various types of bagasse, as for obtaining latex, resin, rubber, essential oils, from guayule plants, can be found, for example, in international patent application WO 2016/062753 in the name of the Applicant mentioned above, or in Italian patent application IT2015000082659 in the name of the Applicant, incorporated herein for reference purposes.

The bagasse derived from guayule plants used in the following examples contained: 18% by weight of cellulose (glucan), 11.6% by weight of xylan, 5.5% by weight of arabinan, 1.5% by weight of galactan and 31% by weight of lignin, with respect to the total weight (dry weight) of the bagasse. The composition of the bagasse derived from guayule plants was determined according to the international standard method defined by the NREL, USA (A. Sluiter et al., NREL/TP-510-42618, revised July 2011 "Determination of Structural Carbohydrates and Lignin in Biomass").

For the purpose of understanding the present invention better and to put it into practice, below are some illustrative and non-limiting examples thereof.

EXAMPLE 1 (COMPARATIVE)

Enzymatic Hydrolysis of Bagasse Derived from Guayule Plants 200 g of bagasse derived from guayule plants (*Parthenium argentatum*), were washed with water, dried in the oven at 60° C. for one night, and ground (particle diameter <2 mm).

Subsequently, in a 500 ml flask, a 10% by weight suspension in water of the aforesaid bagasse with respect to the total weight of the suspension was prepared, to which the enzyme blend Cellic® CTec2 (Novozymes Bioenergy) was added, in the amount of 10% by weight with respect to the loaded bagasse (dry weight) and 100 ml of a 50 mM stock solution of the citrate buffer at pH 5: everything was left, under stirring, (150 rpm), at 50° C., for 72 hours, obtaining a mixture comprising a solid residue comprising lignin and cellulose and a hydrolysate comprising sugars with 6 carbon atoms (C6). After letting everything cool to room temperature (25° C.), said solid residue comprising lignin and cellulose and said hydrolysate comprising monomeric sugars with 6 carbon atoms (C6) were separated by filtration.

Said hydrolysate comprising monomeric sugars with 6 carbon atoms (C6), after concentration through vacuum evaporation (40 mbar, 40° C.), contained 2.05 g of glucose/100 g of bagasse (dry weight) loaded.

The sugar content was determined through ion exchange chromatography (HPAE-PAD), using a Dionex chromatography system, equipped with a Carbopac PA 100 column, with a sodium hydroxide gradient and sodium acetate as counter-ion.

EXAMPLE 2 (INVENTION)

Biological Pretreatment with *Pleurotus ostreatus* of Bagasse Derived from Guayule Plants 200 g of bagasse derived from guayule plants (*Parthenium argentatum*), were washed with water, dried in the oven at 60° C., for one night, and ground (particle diameter <2 mm).

20 g (dry weight) of the aforesaid bagasse, 1 g/l of ammonium nitrate ($NH_4NO_3$), 1 g/l of yeast extract, and 400 ml of a 0.1 M stock solution of phosphate buffer at pH 5.5, were loaded into a 500 ml glass bioreactor, hermetically closed, provided with two inlets for sampling and supplying gases. The mixture obtained was sterilized in an autoclave at 121° C., for 10 minutes. After sterilization, 1 g of *Pleurotus ostreatus* inoculum (wheat flour contaminated with fungi, containing about $10^6$ CFU/g) was added: the suspension obtained was kept, under stirring (250 rpm), at room temperature (25° C.), for 18 days. During such period pure oxygen was flushed into the bioreactor (1 ml/min) for about 60-90 minutes, every 2-3 days and samples were taken on different days after inoculation: 0, 4, 9, 14 and 18, respectively. Each test was carried out three times.

It was observed that monomeric sugars with 6 carbon atoms (C6), including mainly glucose, accumulated gradually in the culture medium (liquid phase) according to a bell-shaped kinetics. The maximum glucose accumulation value, corresponding to 14 culture days, was 28 g of glucose/100 g of bagasse (dry weight) loaded. The sugar content was determined as described in Example 1.

The first solid residue comprising lignin, cellulose and cells of the ligninolytic fungus (mycelium) *Pleurotus ostreatus* obtained, was separated from the suspension by filtration, and was subjected to analysis through the international standard method defined by the NREL specified above. Said analyses confirmed that the quantity of cellulose contained in the solid residue obtained was only slightly lower than that contained in the bagasse (2% reduction) loaded during the biological pretreatment: considering that the quantity of glucose obtained is higher than that theoretically obtainable from the cellulose contained in the initial biomass (see Example 1), it can be concluded that the glucose contained in the culture medium originated from the metabolic activity of the ligninolytic fungus *Pleurotus ostreatus*.

EXAMPLE 3 (INVENTION)

Biological Pretreatment with *Fomitiporia mediterranea* of Bagasse Derived from Guayule Plants 200 g of bagasse derived from guayule plants (*Parthenium argentatum*), were washed with water, dried in the oven at 60° C., for one night, and ground (particle diameter <2 mm).

20 g (dry weight) of the aforesaid bagasse derived from guayule plants, 1 g/l of ($NH_4NO_3$), 1 g/l of yeast extract, and 400 ml of a 0.1 M stock solution of phosphate buffer at pH 5.5, were loaded into a 500 ml glass bioreactor, hermetically closed, provided with two inlets for sampling and supplying gases. The mixture obtained was sterilized in an autoclave at 121° C., for 10 minutes. After sterilization, 1 g of *Fomitiporia mediterranea* inoculum (wheat flour contaminated with fungi, containing about $10^6$ CFU/g) was added: the suspension obtained was kept, under stirring (250 rpm), at room temperature (25° C.), for 18 days. During such period pure oxygen was flushed into the bioreactor (1 ml/min) for about 60-90 minutes, every 2-3 days and samples were taken on different days after inoculation: 0, 4, 9, 14 and 18, respectively. Each test was carried out three times. It was observed that monomeric sugars with 6 carbon atoms (C6), including glucose, accumulated gradually in the culture medium (liquid phase) according to a bell-shaped kinetics. The maximum glucose accumulation value, corresponding to 14 culture days, was 14 g of glucose/100 g of bagasse (dry weight) loaded. The sugar content was determined as described in Example 1.

The first solid residue comprising lignin, cellulose and cells of the ligninolytic fungus (mycelium) *Fomitiporia mediterranea* obtained, was separated from the suspension by filtration, and was subjected to analysis through the international standard method defined by the NREL specified above. Said analyses confirmed that the quantity of cellulose contained in the solid residue obtained was only slightly lower than that contained in the bagasse (1.5% reduction) loaded during the biological pretreatment. It can be concluded that the glucose contained in the culture medium originated from the metabolic activity of the ligninolytic fungus *Fomitiporia mediterranea*.

EXAMPLE 4 (COMPARATIVE)

Enzymatic Hydrolysis of the First Solid Residue Obtained after Biological Pretreatment with *Pleurotus ostreatus* of Bagasse Derived from Guayule Plants The first solid residue obtained after the biological pretreatment with *Pleurotus ostreatus* (Example 2) was washed with water, dried in the oven at 60° C., for one night and finally subjected to enzymatic hydrolysis.

Subsequently, in a 500 ml flask, a 5% by weight suspension in water of said first solid residue with respect to the total weight of the suspension was prepared, to which the enzyme blend Cellic® CTec2 (Novozymes Bioenergy) was added, in the amount of 10% by weight with respect to the first solid residue (dry weight) loaded and 100 ml of a 50 mM stock solution of the citrate buffer at pH 5: everything was left, under stirring, (150 rpm), at 50° C., for 72 hours, obtaining a mixture comprising a solid residue comprising lignin and cellulose and a hydrolysate comprising monomeric sugars with 6 carbon atoms (C6). After letting everything cool to room temperature (25° C.), said solid residue comprising lignin and cellulose and said hydrolysate comprising monomeric sugars with 6 carbon atoms (C6) were separated by filtration.

Said hydrolysate comprising monomeric sugars with 6 carbon atoms (C6), after concentration through vacuum evaporation (40 mbar, 40° C.), contained 2.8 g of glucose/100 g of bagasse (dry weight) loaded. The result therefore suggests that the ligninolytic activity of the fungus *Pleurotus ostreatus* (Example 2) only led to a partial breakdown of the bagasse loaded whose accessibility is increased with respect to the bagasse as such (Example 1) but that still remains incomplete.

EXAMPLE 5 (COMPARATIVE)

Enzymatic Hydrolysis of the First Solid Residue Obtained after Biological Pretreatment with *Fomitiporia mediterranea* of Bagasse Derived from Guayule Plants The first solid residue obtained after the biological pretreatment with *Fomitiporia mediterranea* (Example 3) was washed with water, dried in the oven at 60° C., for one night and finally subjected to enzymatic hydrolysis.

Subsequently, in a 500 ml flask, a 5% by weight suspension in water of said first solid residue with respect to the total weight of the suspension was prepared, to which the enzyme blend Cellic® CTec2 (Novozymes Bioenergy) was added, in the amount of 10% by weight with respect to the first solid residue (dry weight) loaded and 100 ml of a 50 mM stock solution of the citrate buffer at pH 5: everything was left, under stirring, (150 rpm), at 50° C., for 72 hours, obtaining a mixture comprising a solid residue comprising lignin and cellulose and a hydrolysate comprising monomeric sugars with 6 carbon atoms (C6). After letting everything cool to room temperature (25° C.), said solid residue comprising lignin and cellulose and said hydrolysate comprising monomeric sugars with 6 carbon atoms (C6) were separated by filtration.

Said hydrolysate comprising monomeric sugars with 6 carbon atoms (C6), after concentration through vacuum evaporation (40 mbar, 40° C.), contained 3.0 g of glucose/100 g of bagasse (dry weight) loaded. The result therefore suggests that the ligninolytic activity of the fungus *Fomitiporia mediterranea* (Example 3) only led to a partial breakdown of the bagasse loaded whose accessibility is increased with respect to the bagasse as such (Example 1) but that still remains incomplete.

EXAMPLE 6 (COMPARATIVE)

Hydrolysis with Diluted Sulfuric Acid (5% by Weight Aqueous Solution) of Bagasse Derived from Guayule Plants 200 g of bagasse derived from guayule plants (*Parthenium argentatum*), were washed with water, dried in the oven at 60° C., for one night, and ground (particle diameter <2 mm).

Subsequently, 2 g of the aforesaid bagasse and 20 ml of a 5% by weight aqueous solution of sulfuric acid were loaded into a 100 ml glass bottle with a hermetic seal, obtaining a suspension with a pH equal to 0.1: the bottle was placed in an autoclave, at 121° C., for 1 hour, obtaining a mixture comprising a solid residue comprising lignin and cellulose and a hydrolysate prevalently comprising monomeric sugars with 5 carbon atoms (C5) and smaller quantities of monomeric sugars with 6 carbon atoms (C6). After letting everything cool to room temperature (25° C.), said solid residue comprising lignin and cellulose and said hydrolysate prevalently comprising monomeric sugars with 5 carbon atoms (C5) and smaller quantities of monomeric sugars with 6 carbon atoms (C6) were separated by filtration.

Said hydrolysate, prevalently comprising monomeric sugars with 5 carbon atoms (C5) and smaller quantities of monomeric sugars with 6 carbon atoms (C6), after concentration through vacuum evaporation (40 mbar, 40° C.), contained 3.5 g of glucose/100 g of bagasse (dry weight) loaded and 8.2 g of xylose/100 g of bagasse (dry weight) loaded.

EXAMPLE 7 (INVENTION)

Hydrolysis with Diluted Sulfuric Acid (2.5% by Weight Aqueous Solution) of the First Solid Residue Obtained after Biological Pretreatment with *Pleurotus ostreatus* of Bagasse Derived from Guayule Plants The first solid residue obtained after the biological pretreatment with *Pleurotus ostreatus* (Example 2) was washed with water, dried in the oven at 60° C., for one night and finally subjected to enzymatic hydrolysis.

Subsequently, 2 q of the aforesaid bagasse and 20 ml of a 2.5% by weight aqueous solution of sulfuric acid were loaded into a 100 ml glass bottle with a hermetic seal, obtaining a suspension with a pH equal to 0.3: the bottle was placed in an autoclave, at 121° C., for 1 hour, obtaining a mixture comprising a second solid residue comprising lignin and cellulose and a first hydrolysate prevalently comprising monomeric sugars with 5 carbon atoms (C5) and smaller quantities of monomeric sugars with 6 carbon atoms (C6). After letting everything cool to room temperature (25° C.), said second solid residue comprising lignin and cellulose and said first hydrolysate prevalently comprising monomeric sugars with 5 carbon atoms (C5) and smaller quantities of monomeric sugars with 6 carbon atoms (C6) were separated by filtration.

Said first hydrolysate prevalently comprising monomeric sugars with 5 carbon atoms (C5) and smaller quantities of monomeric sugars with 6 carbon atoms (C6), after concentration by vacuum evaporation (40 mbar, 40° C.), contained 3.8 g of glucose/100 g of bagasse (dry weight) loaded and 6.4 g of xylose/100 g of bagasse (dry weight) loaded. Hence, similar yields to those obtained in Example 6 (comparative) were obtained, but using more diluted sulfuric acid (2.5% by weight aqueous solution instead of 5% by weight).

EXAMPLE 8 (COMPARATIVE)

Enzymatic Hydrolysis of the Solid Residue Obtained from Bagasse Derived from Guayule Plants after Hydrolysis with Diluted Sulfuric Acid (5% by Weight Aqueous Solution)

The solid residue obtained after hydrolysis with an aqueous solution of 5% by weight sulfuric acid (Example 6) was washed with water, dried in the oven at 60° C., for one night and finally subjected to enzymatic hydrolysis.

Subsequently, in a 500 ml flask, a 5% by weight suspension in water of said solid residue with respect to the total weight of the suspension was prepared, to which the enzyme blend Cellic® CTec2 (Novozymes Bioenergy) was added, in the amount of 10% by weight with respect to the solid residue (dry weight) loaded and 100 ml of a 50 mM stock solution of the citrate buffer at pH 5: everything was left, under stirring, (150 rpm), at 50° C., for 72 hours, obtaining a mixture comprising a solid residue comprising lignin and cellulose and a hydrolysate prevalently comprising monomeric sugars with 6 carbon atoms (C6) and smaller quantities of monomeric sugars with 5 carbon atoms (C5). After letting everything cool to room temperature (25° C.), said solid residue comprising lignin and cellulose and said hydrolysate prevalently comprising monomeric sugars with 6 carbon atoms (C6) and smaller quantities of monomeric sugars with 5 carbon atoms (C5) were separated by filtration.

Said second hydrolysate comprising monomeric sugars with 5 carbon atoms (C5) and prevalently monomeric sugars with 6 carbon atoms (C6), after concentration through vacuum evaporation (40 mbar, 40° C.), contained 6.0 g of glucose/100 g of bagasse (dry weight) loaded and 0.7 g of xylose/100 g of bagasse (dry weight) loaded.

EXAMPLE 9 (INVENTION)

Enzymatic Hydrolysis of the Second Solid Residue Obtained from Bagasse Derived from Guayule Plants after Biological Pretreatment with *Pleurotus ostreatus* and Hydrolysis with Diluted Sulfuric Acid (2.5% by Weight Aqueous Solution)

The second solid residue obtained after treatment with an aqueous solution of 2.5% by weight sulfuric acid (Example 7) was washed with water, dried in the oven at 60° C., for one night, and finally subjected to enzymatic hydrolysis.

Subsequently, in a 500 ml flask, a 5% by weight suspension in water of said solid residue with respect to the total weight of the suspension was prepared, to which the enzyme blend Cellic® CTec2 (Novozymes Bioenergy) was added, in the amount of 10% by weight with respect to the solid residue (dry weight) loaded and 100 ml of a 50 mM stock solution of the citrate buffer at pH 5: everything was left, under stirring, (150 rpm), at 50° C., for 72 hours, obtaining a mixture comprising a solid residue comprising lignin and cellulose and a second hydrolysate prevalently comprising monomeric sugars with 6 carbon atoms (C6) and smaller quantities of monomeric sugars with 5 carbon atoms (C5). After letting everything cool to room temperature (25° C.), said third solid residue comprising lignin and cellulose and said second hydrolysate prevalently comprising monomeric sugars with 6 carbon atoms (C6) and smaller quantities of monomeric sugars with 5 carbon atoms (C5) were separated by filtration.

Said second hydrolysate prevalently comprises monomeric sugars with 6 carbon atoms (C6) and smaller quantities of monomeric sugars with 5 carbon atoms (C5), after concentration by vacuum evaporation (40 mbar, 40° C.), contained 6.4 g of glucose/100 g of bagasse (dry weight) loaded and 0.7 g of xylose/100 g of bagasse (dry weight) loaded. Hence, similar yields to those obtained in Example 7 (comparative) were obtained, but using diluted sulfuric acid (2.5% by weight aqueous solution instead of 5% by weight). From the examples provided above, it can be deduced the quantities of monomeric sugars with 5 carbon atoms (C5) and of monomeric sugars with 6 carbon atoms (C6) obtained when operating according to a saccharification process in accordance with the process object of the present invention (Example 2, Example 7 and Example 9) with the biological pretreatment and according to a saccharification treatment in accordance with the prior art (Example 6 and Example 8) without the biological pretreatment. As can be observed, if a biological pretreatment in the presence of at least one ligninolytic fungus is inserted, the set of monomeric sugars, comprising both monomeric sugars with 5 carbon atoms (C5) (e.g. xylose, arabinose, galactose) deriving from the degradation of hemicellulose, and monomeric sugars with 6 carbon atoms (C6), in particular glucose, deriving from the degradation of cellulose, or directly produced by the ligninolytic fungus, corresponds to 49.6 g/100 g of bagasse (dry weight) loaded, of which 38.2 g/100 g of bagasse (dry weight) loaded comprises glucose. In the event that the biological pretreatment is not carried out, the set of monomeric sugars, comprising both monomeric sugars with 5 carbon atoms (C5) (e.g. xylose, arabinose, galactose) deriving from the degradation of hemicellulose, and monomeric sugars with 6 carbon atoms (C6), in particular glucose, corresponds to 22.6 g/100 g of bagasse (dry weight) loaded, of which 9.5 g/100 g of bagasse (dry weight) loaded comprises glucose.

The invention claimed is:

1. A process for the production of sugars from biomass derived from guayule plants comprising:
   subjecting said biomass to a biological pretreatment in the presence of at least one ligninolytic fungus obtaining a liquid phase comprising sugars and a first solid residue;
   subjecting said first solid residue to hydrolysis in the presence of at least one diluted inorganic acid obtaining a first hydrolysate comprising sugars and a second solid residue;
   subjecting said second solid residue to enzymatic hydrolysis obtaining a second hydrolysate comprising sugars and a third solid residue.

2. The process for the production of sugars from biomass derived from guayule plants according to claim 1, wherein said biomass derived from guayule plants is the bagasse resulting from the extraction processes to which said guayule plants are subjected.

3. The process for the production of sugars from biomass derived from guayule plants according to claim 1, wherein said at least one ligninolytic fungus is selected from the white rot fungi (WRF) belonging to the strains *Pleurotus ostreatus, Formitiporia mediterranea*; preferably selected from *Pleurotus ostreatus* MUCL 29420, *Formitiporia mediterranea* MUCL 45670.

4. The process for the production of sugars from biomass derived from guayule plants in according to claim 1, wherein said biological pretreatment is carried out:
   at a temperature ranging from 20° C. to 40° C., preferably ranging from 23° C. to 35° C.; and/or
   for a time ranging from 5 days to 25 days, preferably ranging from 10 days to 20 days; and/or
   at a pH ranging from 4.5 to 7, preferably ranging from 5 to 6.7.

5. The process for the production of sugars from biomass derived from guayule plants according to claim 1, wherein said diluted inorganic acid is selected from sulfuric acid, phosphoric acid, or mixtures thereof; preferably said diluted inorganic acid is diluted sulfuric acid, even more preferably it is a 2.5% by weight aqueous solution of sulfuric acid.

6. The process for the production of sugars from biomass derived from guayule plants according to claim 1, wherein said hydrolysis in the presence of at least one diluted inorganic acid is carried out:
   for a time ranging from 30 minutes to 120 minutes, preferably ranging from 45 minutes to 90 minutes; and/or
   at a temperature ranging from 110° C. to 160° C., preferably ranging from 110° C. to 130° C.; and/or
   at a pH ranging from 0.05 to 2, preferably ranging from 0.08 to 1.

7. The process for the production of sugars from biomass derived from guayule plants according to claim 2, wherein said at least one ligninolytic fungus is selected from the white rot fungi (WRF) belonging to the strains *Pleurotus ostreatus, Formitiporia mediterranea*; preferably selected from *Pleurotus ostreatus* MUCL 29420, *Formitiporia mediterranea* MUCL 45670.

8. The process for the production of sugars from biomass derived from guayule plants in according to claim 2, wherein said biological pretreatment is carried out:
   at a temperature ranging from 20° C. to 40° C., preferably ranging from 23° C. to 35° C.; and/or
   for a time ranging from 5 days to 25 days, preferably ranging from 10 days to 20 days; and/or
   at a pH ranging from 4.5 to 7, preferably ranging from 5 to 6.7.

9. The process for the production of sugars from biomass derived from guayule plants in according to claim 3, wherein said biological pretreatment is carried out:
   at a temperature ranging from 20° C. to 40° C., preferably ranging from 23° C. to 35° C.; and/or
   for a time ranging from 5 days to 25 days, preferably ranging from 10 days to 20 days; and/or
   at a pH ranging from 4.5 to 7, preferably ranging from 5 to 6.7.

10. The process for the production of sugars from biomass derived from guayule plants according to claim 2, wherein said diluted inorganic acid is selected from sulfuric acid, phosphoric acid, or mixtures thereof; preferably said diluted inorganic acid is diluted sulfuric acid, even more preferably it is a 2.5% by weight aqueous solution of sulfuric acid.

11. The process for the production of sugars from biomass derived from guayule plants according to claim 3, wherein said diluted inorganic acid is selected from sulfuric acid, phosphoric acid, or mixtures thereof; preferably said diluted inorganic acid is diluted sulfuric acid, even more preferably it is a 2.5% by weight aqueous solution of sulfuric acid.

12. The process for the production of sugars from biomass derived from guayule plants according to claim 4, wherein said diluted inorganic acid is selected from sulfuric acid, phosphoric acid, or mixtures thereof; preferably said diluted inorganic acid is diluted sulfuric acid, even more preferably it is a 2.5% by weight aqueous solution of sulfuric acid.

13. The process for the production of sugars from biomass derived from guayule plants according to claim 2, wherein said hydrolysis in the presence of at least one diluted inorganic acid is carried out:
- for a time ranging from 30 minutes to 120 minutes, preferably ranging from 45 minutes to 90 minutes; and/or
- at a temperature ranging from 110° C. to 160° C., preferably ranging from 110° C. to 130° C.; and/or
- at a pH ranging from 0.05 to 2, preferably ranging from 0.08 to 1.

14. The process for the production of sugars from biomass derived from guayule plants according to claim 3, wherein said hydrolysis in the presence of at least one diluted inorganic acid is carried out:
- for a time ranging from 30 minutes to 120 minutes, preferably ranging from 45 minutes to 90 minutes; and/or
- at a temperature ranging from 110° C. to 160° C., preferably ranging from 110° C. to 130° C.; and/or
- at a pH ranging from 0.05 to 2, preferably ranging from 0.08 to 1.

15. The process for the production of sugars from biomass derived from guayule plants according to claim 4, wherein said hydrolysis in the presence of at least one diluted inorganic acid is carried out:
- for a time ranging from 30 minutes to 120 minutes, preferably ranging from 45 minutes to 90 minutes; and/or
- at a temperature ranging from 110° C. to 160° C., preferably ranging from 110° C. to 130° C.; and/or
- at a pH ranging from 0.05 to 2, preferably ranging from 0.08 to 1.

16. The process for the production of sugars from biomass derived from guayule plants according to claim 5, wherein said hydrolysis in the presence of at least one diluted inorganic acid is carried out:
- for a time ranging from 30 minutes to 120 minutes, preferably ranging from 45 minutes to 90 minutes; and/or
- at a temperature ranging from 110° C. to 160° C., preferably ranging from 110° C. to 130° C.; and/or
- at a pH ranging from 0.05 to 2, preferably ranging from 0.08 to 1.

* * * * *